(12) United States Patent
Byrne et al.

(10) Patent No.: US 8,077,311 B1
(45) Date of Patent: Dec. 13, 2011

(54) SPECTROPHOTOMETRIC SYSTEM FOR SIMULTANEOUS FLOW-THROUGH MEASUREMENTS OF DISSOLVED INORGANIC CARBON, PH AND $CO_2$ FUGACITY

(75) Inventors: Robert H. Byrne, St. Petersburg, FL (US); Eric Kaltenbacher, St. Petersburg, FL (US); Xuewu Liu, Largo, FL (US)

(73) Assignee: University of South Florida, Tampa, FL (US)

( * ) Notice: Subject to any disclaimer, the term of this patent is extended or adjusted under 35 U.S.C. 154(b) by 869 days.

(21) Appl. No.: 12/108,953

(22) Filed: Apr. 24, 2008

Related U.S. Application Data

(60) Provisional application No. 60/913,688, filed on Apr. 24, 2007.

(51) Int. Cl.
*G01J 3/42* (2006.01)
(52) U.S. Cl. ............ 356/319; 356/326; 422/78; 422/62; 436/133; 436/150
(58) Field of Classification Search .................. 356/319, 356/326; 422/78, 62, 80; 436/133, 150, 436/178
See application file for complete search history.

(56) References Cited

U.S. PATENT DOCUMENTS

| | | | |
|---|---|---|---|
| 3,887,281 A | 6/1975 | Kurita et al. | |
| 4,277,343 A | 7/1981 | Paz | |
| 5,132,094 A | 7/1992 | Godec et al. | |
| 5,910,448 A * | 6/1999 | Atwater et al. | 436/133 |
| 5,925,572 A | 7/1999 | Byrne et al. | |
| 5,994,146 A * | 11/1999 | Wright et al. | 436/146 |
| 6,285,807 B1 | 9/2001 | Walt et al. | |
| 6,620,091 B1 | 9/2003 | Zavell et al. | |
| 6,694,157 B1 | 2/2004 | Stone et al. | |
| 2008/0009055 A1 | 1/2008 | Lewnard | |

OTHER PUBLICATIONS

Tapp M.; Hunter K.; Currie K.; MacKaskill B. "Apparatus for continuous-flow underway spectrophotometric measurement of surface water pH." Marine Chemistry. vol. 72. No. 2. Dec. 2000. pp. 193-202.
Todd R. Martz, Jeffrey J. Carr, Craig R. French, and Michael D. DeGrandpre. "A Submersible Autonomous Sensor for Spectrophotometric pH Measurements of Natural Waters." Anal. Chem. 75. 8. pp. 1844-1850, 2003.
M. D. Degrandpre, T. R. Hammar, S. P. Smith and F. L. Sayles. "In Situ Measurements of Seawater pCO2." Limnology and Oceanography. vol. 40. No. 5. Jul. 1995. pp. 969-975.
Byrne R.H.; Liu X.; Kaltenbacher E.A.; Sell K. "Spectrophotometric measurement of total inorganic carbon in aqueous solutions using a liquid core waveguide." Analytica Chimica Acta. vol. 451. No. 2. Jan. 25, 2002. pp. 221-229.
Kenneth M. Johnsona, Arne Kortzingerb, Ludger Mintropc, Jan C. Duinkerb and Douglas W. R. Wallace. "Coulometric total carbon dioxide analysis for marine studies: measurement and internal consistency of underway TCO2 concentrations." Marine Chemistry. vol. 67. Issues 1-2. Oct. 1999. pp. 123-144.

(Continued)

*Primary Examiner* — Layla Lauchman
(74) *Attorney, Agent, or Firm* — Ronald E. Smith; Smith & Hopen, P.A.

(57) ABSTRACT

Provided is a flow-through CO2 system for simultaneously measuring surface seawater pH, carbon dioxide fugacity (fCO2), and total dissolved inorganic carbon (DIC). All measurements are based on spectrophotometric determinations of solution pH at multiple wavelengths using sulfonephthalein indicators.

11 Claims, 12 Drawing Sheets

OTHER PUBLICATIONS

Atsushi Watanabea, Hajime Kayannea, Ken Nozakic, Ken Katoc, Akira Negishic, Setsuko Kudob, Hideshi Kimotod, Masaya Tsudad and Andrew G. Dicksone. "A rapid, precise potentiometric determination of total alkalinity in seawater by a newly developed flow-through analyzer designed for coastal regions." Marine Chemistry. vol. 85. Issues 1-2. Feb. 2004. pp. 75-87.

Richard A. Feely, Rik Wanninkhof, Hugh B. Milburn, Catherine E. Cosca, Mike Stapp and Paulette P. Murphy. "A new automated underway system for making high precision pCO2 measurements onboard research ships." Analytica Chimica Acta. vol. 377. Issues 2-3. Dec. 31, 1998. pp. 185-191.

Taro Takashi, Stewart C. Sutherland, Colm Sweeney, Alain Poisson, Nicolas Metzl, Bronte Tilbrook, Nicolas Bates, Rik Wanninkhof, Richard A. Feely, Chrsitopher Sabine, Jon Olafsson and Yukihiro Nojiri. "Global sea-air CO2 flux based on climatological surface ocean pCO2, and seasonal biological and temperature effects." Deep Sea Research Part II: Topical Studies in Oceanography. vol. 49. Issues 9-10. 2002. pp. 1601-1622.

Zhaohui Aleck Wang, Xuewu Liu, Robert H. Byrne, Rik Wanninkhof, Renate E. Bernstein, Eric A. Kaltenbacher and James Patten. "Simultaneous spectrophotometric flow-through measurements of pH, carbon dioxide fugacity, and total inorganic carbon in seawater." Analytica Chimica Acta. vol. 596. Issue 1. Jul. 16, 2007. pp. 23-36.

* cited by examiner

SPECTROPHOTOMETRIC SYSTEM FOR SIMULTANEOUS FLOW-THROUGH MEASUREMENTS OF DISSOLVED INORGANIC CARBON, PH AND CO$_2$ FUGACITY

CROSS REFERENCE TO RELATED APPLICATIONS

This application is a Non-Provisional Application of co-pending U.S. Provisional Application No. 60/913,688 filed Apr. 24, 2007, which is incorporated herein by reference.

STATEMENT OF GOVERNMENT INTEREST

This invention was made with Government support under NOAA Grants (NA04OAR4310096, AB133R-03-CN-0091, and NA05OAR4601143) to the University of South Florida. The Government has certain rights in the invention.

BACKGROUND OF THE INVENTION

Measurements of four seawater inorganic carbon system parameters—pH, carbon dioxide fugacity (fCO2) or partial pressure of CO$_2$ (p CO$_2$), total dissolved inorganic carbon (DIC), and total alkalinity (TA)—are essential for carbon cycle investigations on both global and local scales. Both observational and modeling efforts rely on high quality inorganic carbon data from field measurements. Extensive efforts have been devoted to improving methodologies and instruments for determination of carbon parameters in seawater.

In standard conventional methodologies, the four core parameters of the seawater inorganic carbon system are measured using diverse instrumentation (e.g. potentiometry, spectrophotometry, gas chromatography, non-dispersive infrared analysis, and coulometry). Recent advances in technology and materials have prompted many researchers to adapt these diverse methodologies for use in unattended in-situ devices and autonomous underway systems without compromising precision and accuracy relative to standard methods (e.g. for in-situ pCO$_2$, underway pCO$_2$, underway pH, in-situ pH, underway DIC and underway TA).

It is preferable for all four parameters of the seawater inorganic carbon system are measured simultaneously and continuously with high temporal resolution, and with high precision and accuracy. Although any two of the four parameters are sufficient to fully characterize the inorganic carbon system via thermodynamic calculations, additional parameters are required to ensure internal consistency of measurements and evaluate the thermodynamic characterizations that relate various CO$_2$ system parameters.

Among all available methodologies for measurements of inorganic carbon species in seawater, spectrophotometric methods are especially promising because they can be used to unify measurements of different parameters and achieve simultaneous multi-parameter measurements at relatively lowcost. Moreover, spectrophotometric methods have many advantageous attributes for measuring inorganic carbon species in seawater: high sensitivity, good stability and selectivity, simplicity, and low rates of sample and reagent consumption.

Spectrophotometric pH measurements using absorbance ratios at multiple wavelengths have long been utilized to obtain precise (±0.0004) discrete shipboard measurements of seawater pH. As such, spectrophotometric pH measurements are approximately an order of magnitude more precise than potentiometric pH measurements. As an additional advantage relative to potentiometric measurements, at-sea spectrophotometric pH measurements do not require calibration subsequent to laboratory characterizations of each indicator's molecular properties as a function of temperature, salinity, pressure and ionic strength. Since pH measurements require very low indicator concentrations (<2_M), pH perturbations due to indicator addition are quite small. Underway spectrophotometric pH measurements can achieve precisions close to those of discrete shipboard spectrophotometric measurements.

Researchers have also developed spectrophotometric sensors for oceanic p CO$_2$ measurements. These sensors have been deployed for measurements on moorings with reported precisions (1-2_atm) close to those obtained in shipboard measurements using a CO$_2$ gas equilibrator with nondispersive infrared analysis. Spectrophotometric p CO$_2$ measurements are generally based on the same principle as those utilized in spectrophotometric pH measurements.

A membrane-optical cell containing a sulfonephthalein indicator functions as a traditional spectrophotometric cell and a CO$_2$ equilibrator. Water samples surround the optical cell but do not have direct contact with the internal indicator solution. CO$_2$ in water samples equilibrates with the cell's internal indicator solution. The resulting pH of the internal solution is measured by a spectrophotometer connected to the cell with optical fibers. The optical cell can be made of polytetrafluoroethylene (PTFE) or silicone, both of which are permeable to CO$_2$ molecules.

Teflon AF 2400 is ideal for spectrophotometric p CO$_2$ measurements because it is highly permeable to CO$_2$ gas molecules, and can be used as a long pathlength liquid core waveguide (LCW). Long pathlengths can improve detection sensitivity, and high CO$_2$ permeability can reduce equilibration times. Byrne et al. described spectrophotometric DIC measurements using Teflon AF 2400 tubing as both an optical cell and a gas permeable membrane. (see R. H. Byrne, X. Liu, E. Kaltenbacher, K. Sell, Anal. Chim Acta 451 (2002) 221; which is incorporated herein by reference). The method is similar to spectrophotometric pCO$_2$ measurement except that water samples are acidified, converting all carbonate species to CO$_2$. Spectrophotometric pH measurements are then used to determine DIC as total CO$_2$ after equilibration across the wall of the LCW.

The procedure is quite simple compared to the coulometric method, and has a comparable precision (1-2 μmol kg$^{-1}$) and accuracy (5 μmol kg$^{-1}$). The reported response time was less than 15 min, which can be further improved by selection of thinner-wall and smaller-diameter capillary tubing. Spectrophotometric DIC measurements are also field portable and easily adapted to in-situ analysis.

What is needed, however, is an autonomous multi-parameter flow-through CO2 system for simultaneous measurement of surface seawater pH, fCO2, and DIC.

SUMMARY OF INVENTION

The invention includes an autonomous multi-parameter flow-through CO$_2$ system for the simultaneous measurement of surface seawater pH, carbon dioxide fugacity (fCO2), and total dissolved inorganic carbon (DIC). In one embodiment, the measurements are based on spectrophotometric determinations of solution pH at multiple wavelengths using sulfonephthalein indicators. The pH optical cell of this embodiment is machined from a PEEK polymer rod bearing a bore-hole with an optical pathlength of ~15 cm. The fCO$_2$ optical cell consists of capillary tubing sealed within the bore-hole of a PEEK rod.

The tubing is filled with a standard indicator solution with a fixed total alkalinity, and forms a liquid core waveguide (LCW). The LCW functions as both a long pathlength (~15 cm) optical cell and a membrane that equilibrates the internal standard solution with external seawater. Fugacity ($fCO_2$) is determined by measuring the pH of the internal solution. DIC is measured by determining the pH of standard internal solutions in equilibrium with seawater that has been acidified to convert all forms of DIC to $CO_2$. The system runs repetitive measurement cycles with a sampling frequency of ~7 samples (21 measurements) per hour. The invention integrates spectrophotometric measurements of multiple $CO_2$ parameters into a single package suitable for observations of both seawater and freshwater.

The invention includes a multi-parameter spectrophotometric flow-through $CO_2$ system capable of simultaneously measuring surface seawater $fCO_2$, DIC, and pH with high sensitivity, and consistency with current state-of-the-art measurements. The invention incorporates a modular design, allowing additional channels dedicated to other chemical properties to be incorporated conveniently. For example, a total alkalinity (TA) channel can be incorporated whereby all four parameters of the inorganic carbon system can be measured based on spectrophotometric principles. A dedicated for monitoring monitor atmospheric $fCO_2$ uses the same reagents required for seawater $fCO_2$ measurements. Atmospheric $fCO_2$ is determined by measuring an uncontaminated air stream pumped through the sample-passage of the $fCO_2$-air channel.

The invention can be adapted for deployments on moorings or other platforms in addition to the underway embodiment discussed below. The invention makes underway measurements at a constant temperature using a large thermostated water bath.

The invention also provides for 'calibration free' measurements of $fCO_2$ and DIC, using indicator solutions with a constant composition (i.e. fixed, well-defined total alkalinity). Proper storage of indicator solutions that have been calibrated in the laboratory eliminates the necessity of $fCO_2$ and DIC calibrations at sea.

The quality of $fCO_2$, DIC, and pH measurements obtained with the current underway system is comparable to that obtained with established standard methods. Given the sampling costs and complexity of current conventional analytical methods, wherein each $fCO_2$-system measurement requires approximately two shipboard personnel, automated systems are beneficial to oceanic carbon studies.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

The invention includes an automated multi-parameter flow-through $CO_2$ system with a plurality of seawater channels that simultaneously measure surface seawater pH, $fCO_2$, and DIC. The system can operate continuously and measure three parameters at a constant temperature (25° C.) every ~8 min (~7 samples per hour). The main sub-units of the system include optical system (optical cells, light sources, and spectrometers etc.), flow control system (peristaltic pumps and valves etc.), and the electronic control system. Measurement temperature is controlled by an integrated thermostat. Additional components include a pressure transmitter for measurements of atmospheric pressure, and a conductivy/temperature/depth (CTD) profiler.

Direct spectrophotometric measurements of seawater pH are obtained with a small bore-hole PEEK (Polyetheretherketone) rod. By continuously mixing water sample and indicator solution, pH can be measured in real-time. Teflon AF 2400 capillary tubing was used as both an LCW and a gas-equilibrium membrane cell for $fCO_2$ and DIC measurements. A sulfonephthalein indicator with constant total alkalinity (dissolved $Na_2CO_3$) serves as the liquid core of the Teflon LCW tubing, and water samples (acidified water samples for DIC measurements) are directed to flow externally. After equilibration across the $CO_2$ permeable Teflon AF membrane, the $fCO_2$ of the internal solution and the external sample are identical. DIC and $fCO_2$ are determined through spectrophotometric measurements of internal solution pH. Depending on the desired pH range of the internal solutions, different indicators and total alkalinities are chosen for $fCO_2$ and DIC. For underway measurements, the parameters are measured at a thermostated temperature (25° C.).

Figure 1:
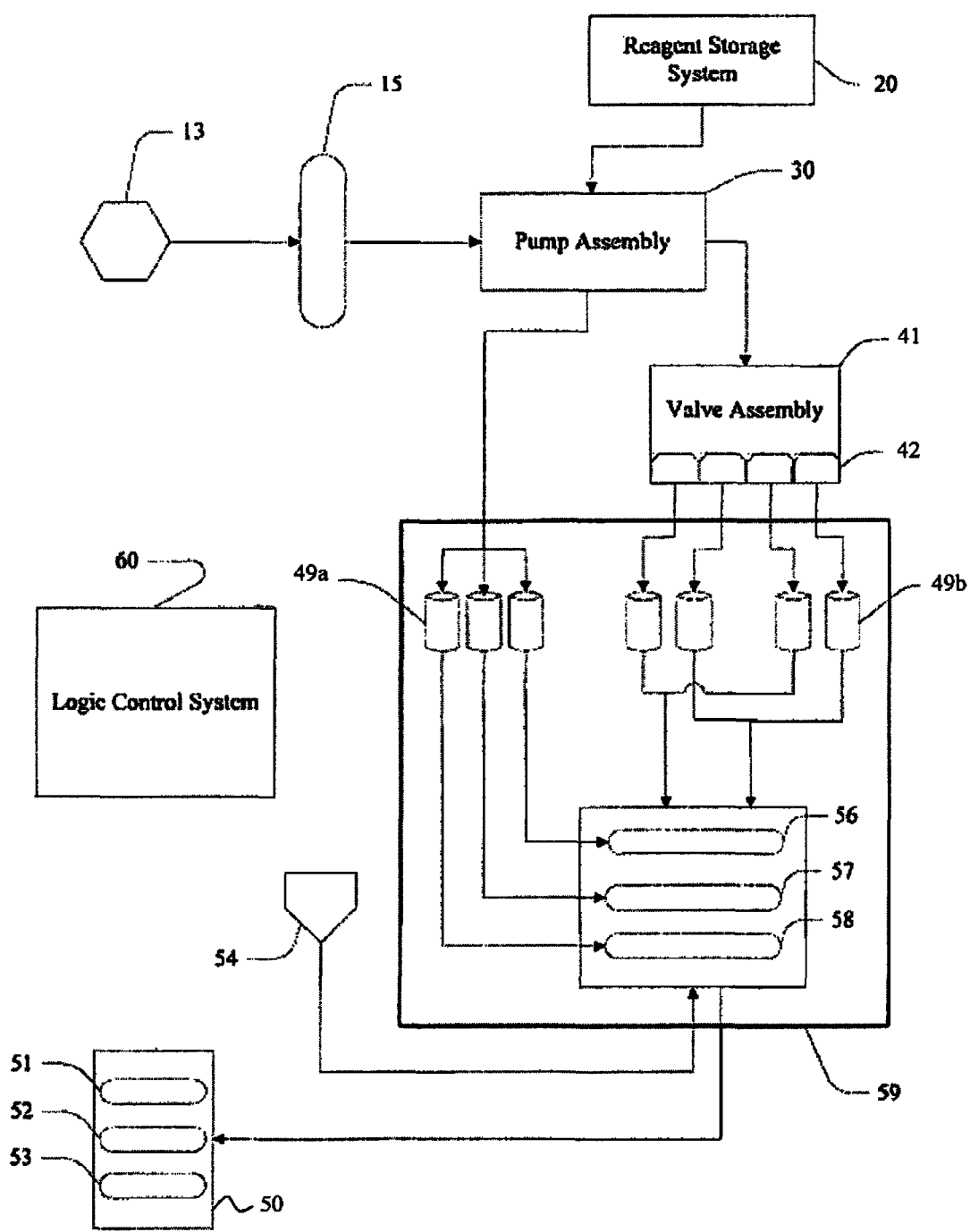
FIG. 1 is a block diagram of the spectrophotometric multi-parameter flow-through $CO_2$ system.

An illustrative embodiment of the invention is shown in FIG. 1. The flow control system of this embodiment includes sample filter 13, CTD 15, reagent storage system 20, pump assembly 30, valve assembly 42, debubbling assembly 43, solution equilibrating coils 44 and sample equilibration coils 46. The optical system includes $fCO_2$ spectrometer 51, DIC spectrometer 52, pH spectrometer 53, light source 54, pH cell 56, DIC cell 57 and $fCO_2$ cell 58. Thermostated chamber 59 houses the optical cells (56, 57 and 58) as well as the associated plumbing, including solution equilibrating coils 44 and sample equilibration coils 46. Control system 60 communicates with all components and logs the data from the three measurement channels. Having described the structure of the multi-parameter flow-through $CO_2$ system generally, the components of specific embodiments of the invention will be discussed in greater detail.

Flow Control System

Figure 2:
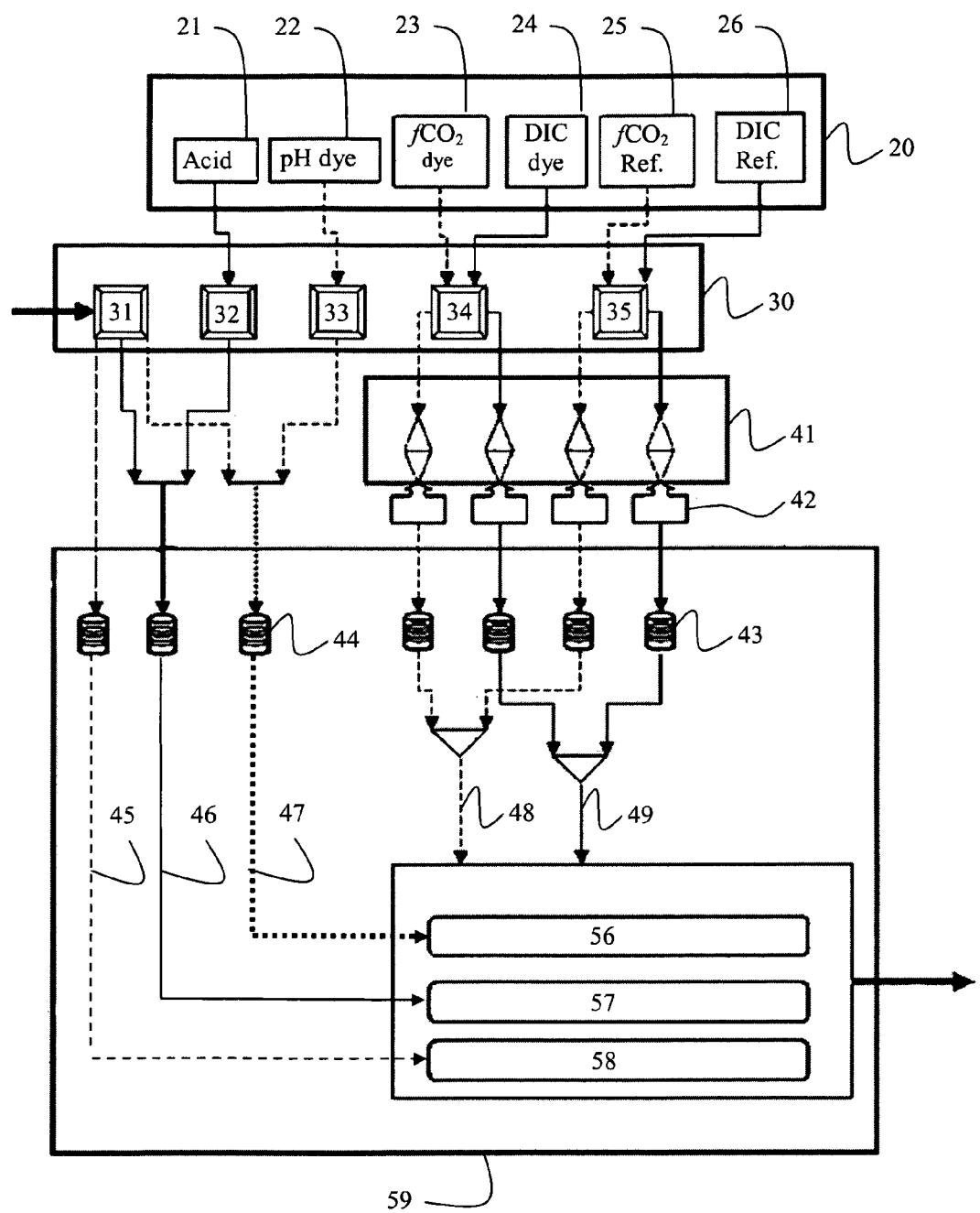
FIG. 2 is a block diagram of the flow control of the spectrophotometric multi-parameter flow-through $CO_2$ system.

FIG. 2 illustrates the flow control system of one embodiment of the invention. Water samples, reference solutions, indicator solutions, and the acid solution are delivered to the system using a plurality of peristaltic pumps. The plurality of pumps include sample pump 31, acid pump 32, pH dye pump 33, carbon die pump 34 and carbon reference pump 35. Sample pump 31 is disposed in fluid communication between CTD (not shown) and pH cell 56 (through pH sample input 46), DIC cell 57 (through DIC sample input 47) and $fCO_2$ cell 58 (through $fCO_2$ sample input 48). Acid pump 32 is disposed in fluid communication between acid reservoir 21 and DIC cell 57 (through DIC input 47). pH dye pump 33 is disposed in fluid communication between pH dye reservoir 22 and pH cell 56 (through pH input 46).

Carbon dye pump 34 is disposed in fluid communication between $fCO_2$ dye reservoir 23 and $fCO_2$ cell 58 (through $fCO_2$ reagent input 43) as well as between DIC dye reservoir 24 and DIC cell 57 (through DIC reagent input 44). Lastly, carbon reference pump 35 is disposed in fluid communication between $fCO_2$ reference reservoir 25 and $fCO_2$ cell 58 (through $fCO_2$ reagent input 43) as well as between DIC reference reservoir 26 and DIC cell 57 (through DIC reagent input 44).

In operation water passes through a plastic plate filter to remove large suspended particles, the water sample flows into the bottom port of the CTD housing and discharges from the top port. Water samples are drawn from a middle port of the housing by sample pump 31, and distributed to $fCO_2$ sample input 48, DIC sample input 47 and pH sample input 46. Acid pump 32 injects hydrochloric acid (HCl, ~2.5 M) from acid reservoir 21 into the sample DIC sample input 47 through a "T" connector to acidify samples for DIC measurement. An in-line mixer (such as a plastic coil inserted in the tubing) is used to mix the sample with HCl after the "T" connector. The mixing ratio (seawater to HCl) is maintained at ~700:1. The pH water sample mixes with the pH indicator solution delivered by the pH dye pump with a mixing ratio of ~700:1. Another in-line mixer is used to facilitate further mixing. The sample leading through $fCO_2$ sample input 48 is not mixed with any reagent.

Sample-thermal equilibration coils (49a) are disposed along each sample input before the three lines of water samples flow through the three optical cells. Chemically inert tubing which possesses good gas impermeability, such as PEEK and ParMed® tubing, are preferably used for plumbing downstream from the CTD to minimize possible contamination of samples and reagents.

Valve assembly 41 includes a plurality of two-way solenoid valves adapted to stop the flow of reagents from the reference and dye reservoirs while the $fCO_2$ and DIC optical cells are in use. A plurality of debubblers (42) are located downstream from valve assembly 41 to remove air bubbles from the streams of reference and dye solutions.

The optical cells and their associated plumbing are all located inside thermostated water bath 59 to maintain a constant measurement temperature (i.e. 25.0±0.1° C.). The $fCO_2$/DIC reference and dye solutions pass through reagent temperature equilibrating coils 49b before entering $fCO_2$ cell 58 (through $fCO_2$ reagent input 43) and DIC cell 57 (through DIC reagent input 44).

Optical System

Three miniature fiber optic spectrometers (pH spectrometer 51, DIC spectrometer 52 and $fCO_2$ spectrometer 53) are used to detect optical signals from the corresponding optical cells. In the embodiment used to generate the data disclosed below, each spectrometer was equipped with a 2048-element CCD array capable of spectral observations between 200 and 1100 nm with an optical resolution of 0.33 nm. The spectrometers are housed in thermostated chamber 50 to overcome the signal drift that may occur as a result of thermal changes during long-term use. Thermostated chamber 50 regulates temperature to 18±1° C.

Figure 3A:
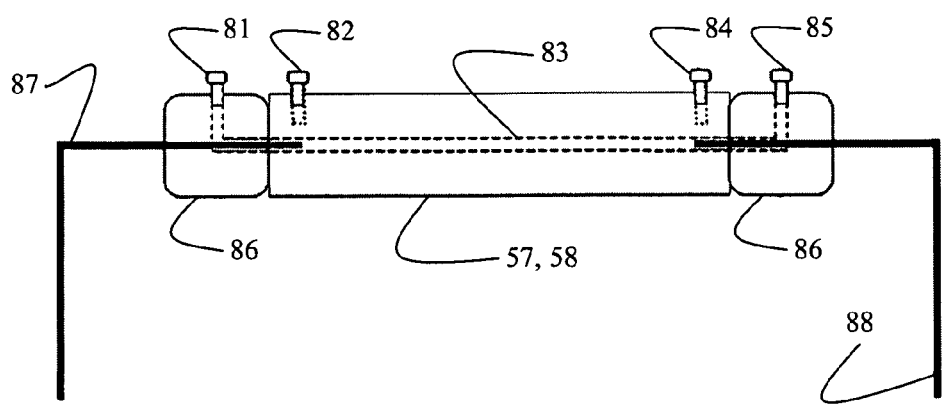
FIG. 3A is diagram of the $fCO_2$ and DIC optical cells.
Figure 3B:
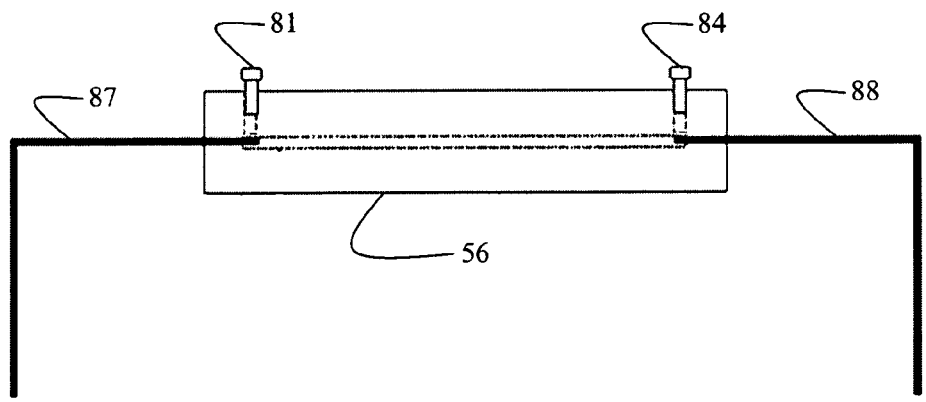
FIG. 3B is diagram of an optical cell.

In this example, $fCO_2$ cell 58 and DIC cell 57 were fabricated from PEEK rods. The centerpiece of the $fCO_2$ and IC cell had a 27 mm O.D. and a 2 mm I.D. with a length of 15 cm. A Teflon AF 2400 Liquid Crystal Waveguide (LCW) (0.5 mm O.D.×0.4 mm I.D., Biogeneral, CA) was disposed inside this centerpiece. Structure of the optical cells is FIGS. 3A and 3B. The centerpiece of the $fCO_2$ cell 58 and DIC cell 57 (FIG. 3A) are equiped sample inlet 81, reagent inlet 82 with outlet 85 and reagent outlet 84 on the opposite side of LCW 83. A first optical fiber (87) connects the optical cell with the light source (not shown) and a second optical fiber (88) connects the optical cell with the corresponding spectrophotometer. The optical fibers are inserted into the ends of LCW 83 through PEEK connectors 86. The ends of LCW 83 are sealed by O-rings housed inside connectors 86. PEEK connectors 86 allow both reagent and light to pass through LCW 83. The pH optical cell (FIG. 3B) is also machined from a PEEK rod, but does not require special connectors since no LCW is used.

Light source 54 (FIGS. 1 and 2), such as a high-temperature tungsten lamp, is connected to each optical cell. For all spectrophotometric measurements of CO2 parameters, measurement precision is strongly affected by the output spectrum of the light source. A uniform output of light between 430 and 700 nm is desirable for optimal signal-to-noise ratios. However, widely used tungsten or incandescent lamps have a limited light output at wavelengths around 430 nm (absorbance maximum for the HI-indicator form). Consequently, an assembly employing blue and short-pass filters was used to achieve an improved balance of spectral intensity between 430 and 700 nm

Electronic Control System

Electronic control system 60 (FIG. 1) comprises of a power supply, a relay board and a personal computer. Light sources, spectrophotometers, CTD, pressure transducer (for measurement of air pressure), pumps, and switch valves are connected to the control system. The computer controls communication with all components and logs the data from the three measurement channels. The communication interface software, has a user-definable interface that allows users to set up command sequences to continuously run the multi-parameter flow-through $CO_2$ system and store data from measurements in an automated mode. A manual "user mode" allows operators to initialize the system, adjust light level, set operation parameters, and check the stability of the system.

Measurement of pH

Spectrophotometric pH measurements have been well established as a standard method for seawater $CO_2$ system measurements. Within the normal pH range of seawater, dissociation of sulfonephthalein indicators ($H_2I$) in solution is dominated by the following equilibrium:

$$HI^- \xrightleftharpoons{K_I} H^+ + I^{2-} \tag{1}$$

where $K_I$ is an indicator dissociation constant. Solution pH can then be written as:

$$pH = pK_I + \log\frac{[I^{2-}]}{[HI^-]} \tag{2}$$

where brackets ([ ]) denote the concentrations of indicator species, $K_I=[H^+][I^{2-}][HI^-]^{-1}$, and $pK_I=-\log K_I$.

Equation 2 can be written in terms of $pK_I$ and an indicator absorbance ratio, $R={_{\lambda_2}}A/{_{\lambda_1}}A$, where $\lambda_1$ and $\lambda_2$ are the wavelengths for the absorbance maxima of $HI^-$ and $I^{2-}$ [11]:

$$pH = pK_I + \log\frac{R - e_1}{e_2 - Re_3} \tag{3}$$

The coefficients $e_1$, $e_2$, and $e_3$ are indicator molar absorbance ratios at wavelengths $\lambda_1$ and $\lambda_2$:

$$e_1 = \frac{{_{\lambda_2}}\epsilon_{HI}}{{_{\lambda_1}}\epsilon_{HI}}, \quad e_2 = \frac{{_{\lambda_2}}\epsilon_{I}}{{_{\lambda_1}}\epsilon_{HI}}, \quad e_3 = \frac{{_{\lambda_1}}\epsilon_{I}}{{_{\lambda_1}}\epsilon_{HI}} \tag{4}$$

where ${_{\lambda_1}}\epsilon_I$ and ${_{\lambda_2}}\epsilon_I$ denote the molar absorbances of $I^{2-}$ at wavelengths $\lambda_1$ and $\lambda_2$, and ${_{\lambda_1}}\epsilon_{HI}$ and ${_{\lambda_2}}\epsilon_{HI}$ refer to the molar absorbances of $HI^-$ at wavelengths $\lambda_1$ and $\lambda_2$. Equation 3 shows that spectrophotometric pH measurements require calibration of indicator molecular properties in the laboratory ($pK_I$, $e_1$, $e_2$, and $e_3$ and their variation with temperature, salinity, pressure), but do not require subsequent calibration in the field. Measurements in the field can then be termed as "calibration free" [11, 21].

Seawater pH is determined on the total hydrogen ion concentration scale ($pH_T$):

$$pH_T = -\log[H^+]_T = -\log[H^+] - \log\left(1 + \frac{S_T}{K_{HSO_4}}\right) \tag{5}$$

where [H$^+$] refers to the free hydrogen ion concentration, $S_T$ is the total sulfate concentration, and $K_{HSO_4}$ is the $HSO_4^-$ dissociation constant. Equation 3 is then written as:

$$pH_T = -\log_T K_I + \log\frac{R - e_1}{e_2 - Re_3} \tag{6}$$

For surface seawater $pH_T$ determinations, thymol blue is used for direct pH measurements, whereby $\lambda_1 = 435$ nm and $\lambda_2 = 596$ nm. A third wavelength, $\lambda_{ref} = 700$ nm, is used to compensate for potential baseline shifts between blank and sample measurements.

$$-\log_T K_I = \frac{4.706S}{T} + 26.3300 - 7.17218 \log T - 0.017316S \tag{7}$$

$e_1 = -0.00132 + 1.6\times10^{-5}T$, $e_2 = 7.2326 - 0.0299717T + 4.6\times10^{-5}T^2$, and $$e_3 = 0.0223 + 0.0003917T, \tag{8}$$

where S denotes salinity of the sample and T denotes the absolute temperature in degrees Kelvin.

Measurement of $fCO_2$

For spectrophotometric $fCO_2$ measurements, the internal standard solution of the LCW comprises a $Na_2CO_3$-indicator solution with a constant total alkalinity (TA). Upon equilibration, the $fCO_2$ in sample waters is equal to the $fCO_2$ of the internal solution:

$$(fCO_2)_{ex} = f(CO_2)_i, \tag{9}$$

where subscripts 'ex' and 'i' refer to external samples and internal standard solution.

At equilibrium, species concentrations in the internal solution are expressed in terms of the dissociation constants of carbonic acid as follows:

$$K_1' = \frac{[H^+][HCO_3^-]}{[CO_2^*]} \tag{10}$$

$$K_2' = \frac{[H^+][CO_3^{2-}]}{[HCO_3^-]} \tag{11}$$

$$[CO_2^*] = [CO_2] + [H_2CO_3] = K_0(fCO_2)_i \tag{12}$$

where $K_0$ is the Henry's Law constant. The titration alkalinity of the internal $Na_2CO_3$-indicator solution can be written as:

$$TA = 2[CO_3^{2-}] + [HCO_3^-] + [I^{2-}] + [OH^-] - [H^+] \tag{13}$$

Combining Equations 10-12, Equation 13 can be rearranged and expressed in terms of $(fCO_2)_i$:

$$(fCO_2)_i = \frac{TA - ([I^{2-}] + [OH^-] - [H^+])}{2K_0K_1'K_2'[H^+]^{-2} + K_0K_1'[H^+]^{-1}} \tag{14}$$

Since $TA \gg [I^{2-}] + [OH^-] - [H^+]$, Equation 14 can be written as:

$$(fCO_2)_i = (fCO_2)_{ex} = \frac{TA}{2K_0K_1'K_2'[H^+]^{-2} + K_0K_1'[H^+]^{-1}} = \frac{TA}{L} \tag{15}$$

where $L = 2K_0K_1'K_2'[H^+]^{-2} + K_0K_1'[H^+]^{-1}$.

Using Equation 15, (fCO$_2$), can be calculated from the pH of the internal solution, as all other terms are constants at constant temperature.

Phenol red ($\lambda_1$=434 nm, $\lambda_2$=558 nm, and $\lambda_{ref}$=700 nm) is used as the indicator for measurements of fCO$_2$. The fCO$_2$ measurement system is calibrated using CO$_2$ gases at known concentrations. The pH of the indicator solution is determined spectrophotometrically, and the L term in Equation 15 is then calculated. Since the TA of the internal solution is constant (but not necessarily and accurately known), sample fCO$_2$ has a linear dependence on 1/L at constant temperature:

$$(fCO_2)_{ex} = \frac{a}{L} + b \quad (16)$$

The calibration constants, a and b, account for all uncertainties in Equation 15 including the absolute value of TA.

Measurement of DIC

Spectrophotometric measurements of DIC using liquid core waveguides have been described previously. Water samples are acidified before measurements (pH≈2.7), whereupon the total CO*$_2$ concentration equals the DIC concentration. After the internal Na$_2$CO$_3$-indicator solution attains CO$_2$ equilibrium with the acidified water samples across the LCW CO$_2$-permeable walls, the CO$_2$ fugacity of the acidified outer solution can be written as:

$$(fCO_2)_{ex} = (fCO_2)_i = \frac{DIC}{(K_0)_{ex}}, \quad (17)$$

where the subscript "ex" refers to the acidified outer solution, and "i" indicates the internal solution. Sample DIC concentration then can be derived from observations of the internal solution by combining Equation 17 with Equations 10 and 12:

$$DIC = \left(\frac{(K_0)_{ex}}{(K_0)_i}\right)[H^+]_i \frac{[HCO_3^-]_i}{K_1'} \quad (18)$$

Using Equation 18, the DIC concentration is directly linked to the pH of the internal solution, which can be measured spectrophotometrically with an appropriate sulfonephthalein indicator. At equilibrium, with internal solution pH between 5.6 and 6.4 for DIC concentrations between 1000 and 3000 µmol kg$^{-1}$, bromocresol purple (BCP, $\lambda_1$=432 nm, $\lambda_2$=589 nm, and $\lambda_{ref}$=700 nm) with a pK$_I$ near 6.5 [22] is ideal for observations of pH. Within the 5.6 to 6.4 pH range, the TA of the internal Na$_2$CO$_3$-indicator solution can be simplified relative to Equation 13:

TA=[HCO$_3^-$]+[I$^{2-}$]−[H$^+$]$_i$, and $$[HCO_3^-]=TA+[H^+]_i-[I^{2-}] \quad (19)$$

Combining Equations 3, 18 and 19, DIC can be expressed as:

$$\log DIC = \log\left(\frac{(K_0)_a}{(K_0)_i}\right) + \quad (20)$$
$$\log(TA + [H^+] - [I^{2-}]) + \log\left(\frac{K_1 e_2}{K_1'}\right) - \log\left(\frac{R - e_1}{1 - Re_3/e_2}\right)$$

$$\frac{(K_0)_a}{(K_0)_i}$$

can be calculated from the known dependence of Henry's Law (gas solubility) constants on temperature and ionic strength. CO$_2$ solubility constants in freshwater and seawater can be expressed as:

$$\ln K_0 = 93.4517\left(\frac{100}{T}\right) - 60.2409 + 23.3585 \ln\left(\frac{T}{100}\right) + \quad (21)$$
$$50.20\mu\left(0.023517 - 0.023655\left(\frac{T}{100}\right) + 0.0047036\left(\frac{T}{100}\right)^2\right),$$

where µ is the ionic strength of the solution. Consequently, $$\log\left(\frac{(K_0)_a}{(K_0)_i}\right)$$

is given as:

$$\log\left(\frac{(K_0)_a}{(K_0)_i}\right) = \quad (22)$$
$$\left(\frac{50.20(\mu_a - \mu_i)}{2.303}\right)\left(0.023517 - 0.023655\left(\frac{T}{100}\right) + 0.0047036\left(\frac{T}{100}\right)^2\right)$$

The term $$\log\left(\frac{K_1 e_2}{K_1'}\right)$$

in Equation 20 is constant for a solution at constant temperature. If TA≧1000 µmol kg$^{-1}$ for the internal solution, the term (TA+[H$^+$]−[I$^{2-}$]) varies by no more than 0.06% for DIC concentrations between 1000 and 3000 µmol kg$^{-1}$. As such, the second and third terms in Equation 20 can be combined and treated as a single temperature dependent constant. DIC is finally expressed as:

$$\log DIC = \log\left(\frac{(K_0)_a}{(K_0)_i}\right) + B - \log\left(\frac{R - e_1}{1 - Re_3/e_2}\right) \quad (23)$$

where B is an experimentally derived calibration constant.

EXAMPLES

The following represents examples which illustrate procedures for practicing the invention. All proportions, volumes and/or concentrations were presented by way of example and should not be construed as limiting.

Reagents and Storage

Sodium salts of phenol red (fCO2 measurement) and bromocresol purple (DIC measurement) (Sigma-Aldrich, ACS Certified) were dissolved in Milli-Q water to make 4-8 mM indicator (dye) stock solutions. The indicator stock solutions were stored in opaque glass bottles at room temperature. The R ratios of the indicator stock solutions were adjusted to ~1.0 with 1N NaOH or HCl solution to minimize indicator-induced pH perturbations.

fCO$_2$ and DIC dyes: The working indicator solutions for fCO$_2$ and DIC measurements were prepared from indicator stock solutions in Milli-Q water within 20 L glass bottles. Final indicator concentrations in the working solutions were ~2 μM for both phenol red and bromocresol purple. The total alkalinity of the indicator solutions was established by addition of ultra-purified $Na_2CO_3$ (J. T. Baker, Ultrex Ultrapure). The final total alkalinity of the indicator solutions was near 225 and 1000 μmol $kg^{-1}$ for $fCO_2$ and DIC measurements, respectively. Total alkalinity values were chosen based on calculations to insure that indicator solutions were suitable for measurements with a wide range of $fCO_2$ and DIC.

Finally, 10 mL of 10% lauryl sulfate sodium salt solution was added to each bottle of indicator solution. Lauryl sulfate functions as a surfactant to overcome the hydrophobic properties of sulfonephthalein indicators, which may create non-ideal behavior in conjunction with use of Teflon AF to measure pH. The surfactant also serves to clean the LCW surfaces.

$fCO_2$ and DIC reference solutions: Reference solutions for $fCO_2$ and DIC measurements were prepared using identical procedures but without added indicators. The working indicator and reference solutions for $fCO_2$ and DIC measurements were enclosed in 4 L (maximum capacity) gas-impermeable laminated bags (Pollution Measurement Corporation) before use. The bag consisted of an inner layer of Teflon FEP film and an outer layer of aluminum. The bags also eliminate light intrusion. Bagged solutions were refrigerated at 4-7° C. before use and all measurements and calibrations were performed in an air-conditioned room. Under such conditions, laboratory tests show that bagged solutions can last at least a month without appreciable changes of composition. The 2.5M HCl used for acidifying DIC samples was prepared by diluting concentrated HCl (Baker, ACS Certified) with Milli-Q water. This acid was stored in 500 mL glass bottles.

pH dye: For pH measurements, the sodium salt of thymol blue (Sigma-Aldrich, ACS Certified) was used to make working indicator solutions with concentrations between 1.5-2.0 mM. The R ratio of each indicator solution was adjusted (R~0.77) to minimize the magnitude of indicator-induced pH perturbations. Each pH indicator solution was stored in 500 mL gas-impermeable laminated bags. No surfactant was added to these indicator solutions as it was not required in conjunction with use of PEEK tubing.

With the established sample/indicator mixing ratio, the final thymol blue concentration in the pH measurement cell was ~2-3 μM. For the pH range encountered in this work, indicator perturbations were generally smaller than ±0.001, which was within the precision of the instrument.

Calibration

The $fCO_2$ channel was calibrated with several air-balanced $CO_2$ gas standards (Airgas) providing $fCO_2$ values between 257 and 809 μatm. These were initially calibrated against a high-accuracy air-balanced CO2 standard (454.77±0.04 μatm) obtained from the Climate Monitoring Division of Earth System Research Laboratory (ESRL) of NOAA at Boulder, Colo. These calibrations were conducted using a Li—COR 7000CO2/H2O analyzer with a precision better than ±1.0 μatm. The gas flow rate was controlled at 30 $mLmin^{-1}$ using a mass flow controller.

The $fCO_2$ channel was connected directly to each standard $CO_2$ gas cylinder during calibration. Each standard gas flowed through a large copper coil placed inside the thermostated water bath. The sample chamber of the $fCO_2$ channel was flushed with dry gas before calibration to remove any water vapor. The slope, a, and the intercept, b, in Eq. (16) were derived from calibrations with each batch of phenol red solution.

The DIC channel was calibrated against the Certified Reference Material (CRM) from Dr. A. G. Dickson at the Scripps Institution of Oceanography, La Jolla, Calif. to obtain the constant (B) in Eq. (23) for a particular batch of bromocresol purple solution. All other constants were obtained from literature.

The thymol blue used for pH measurements does not require calibration since all inherent characteristics of thymol blue have been established previously. As long as the compositions (total alkalinity) of the indicator solutions (phenol red and bromocresol purple) used for fCO2 and DIC measurements do not change, re-calibration is not required during field measurements. However, since changes in the total alkalinity of indicator solutions can be encountered unexpectedly (e.g. due to mechanically compromised reagent bags), indicator solutions were periodically monitored during field measurements for consistency with laboratory calibrations. Recalibration was implemented as necessary. For the test cruise, the indicator solutions for $fCO_2$ and DIC measurements were checked for calibration consistency by measuring a NOAA $CO_2$ standard and a DIC standard (CRM) just prior to embarkation and every 3-4 days during the cruise.

The initial onboard check revealed that $fCO_2$ readings were different from calibrations in the laboratory. This may have resulted from $fCO_2$ indicator solution composition changes during transportation. The $fCO_2$ channel was therefore re-calibrated using four $CO_2$ gas standards (NOAA) during transit to the first station. No statistically significant changes in calibration were detected for any indicator reagent bag during the cruise. Between bags, however, calibration consistency checks sometimes revealed 2-3% differences. It was suspected that minor contamination may have occurred when solutions were dispatched from large glass bottles to the reagent bags. In such cases, the $fCO_2$ channel was fully recalibrated using four $CO_2$ gas standards (NOAA).

Operational Procedures

During operation the interface software runs a repetitive sequence of commands to the multi-parameter flow-through CO2 system as summarized below:

(1) All solenoid valves are initialized. Lights are turned on for stabilization (~10 min).

(2) The sample and acid pumps are activated (<1 s).

(3) Seawater is continuously flushed through all measurement channels. For the pH channel, seawater without thymol blue serves as an absorbance reference (~2 min).

(4) Solenoid valves associated with the $fCO_2$ and DIC reference solutions (reagent solutions with no added indicators) are opened. The carbon reference pump is turned on to flush reference solutions through the $fCO_2$ and DIC channels (~3 min).

(5) Solenoid valves are closed. References for all three channels are recorded and logged (~0.5 min).

(6) The pH dye pump is turned on and thymol blue solution is injected into the seawater sample stream (<1 s).

(7) Solenoid valves associated with the $fCO_2$ and DIC indicator solutions are opened. The carbon dye pump injects indicator solutions into the $fCO_2$ and DIC channels. Seawater samples for pH measurements mix with thymol blue (1.5-3 min).

(8) Solenoid valves are closed. $fCO_2$ and DIC samples equilibrate with the indicator solutions across the LCW (~7 min).

(9) All measurements are recorded (~10 s).

(10) Steps 7-9 are repeated five times.

(11) The pH dye pump is stopped (<1 s).

(12) One measurement cycle ends. The sequence repeats from Step 3.

A single measurement cycle requires about 1 hour before new references are taken for the next cycle. The current measurement frequency is 7-8 samples per hour for each parameter. It is noted that pH measurements can have much higher measurement frequency because pH indicator equilibration is instantaneous.

A lower measurement frequency for the pH channel was chosen in this example to match $fCO_2$ and DIC measurement frequencies. During calibration of the phenol red solution for $fCO_2$ measurements, the $fCO_2$ sample line was disconnected and rinsed with Milli-Q water. $CO_2$ standard gas was then passed through the sample-passage external to the $fCO_2$ LCW. For DIC measurements, CRM (instead of seawater) was directed through the DIC channel for calibration of the bromocresol purple solution.

The above running sequence did not change during calibration. Switches between samples and calibration materials were made manually.

Sample and Reagent Consumption

Advantageously, the multi-parameter flow-through $CO_2$ system of the current invention consumes small quantities of samples and reagents during measurements. With the foregoing sample pump settings, each measurement channel only consumes ~10 mL of seawater per minute. For the indicator and reference solutions used during fCO~ and DIC measurements, the consumption rate with the foregoing running sequence is ~12 $mLh^{-1}$. Each $fCO^2$/DIC indicator or reference bag then provides 10-14 days of uninterrupted measurements. With mixing ratios of ~700 for both pH measurements and acidification of DIC samples, the consumption rate for HCl and pH indicator solution is 10 µL $min_{-1}$. A 500 mL bottles of HCl or pH indicator solution thus permits continuous measurements for a period of 1 month.

Underway Measurements

The invention was tested between Punta Arenas, Chile and Fortaleza, Brazil. The test transect was meridional from 60° S to 2° S in the western South Atlantic Ocean (FIG. 34). A total of 121 CTD/Rosette stations were occupied.

$CO_2$ system parameters for surface water were measured by different research groups using established methodseither continuously (underway $fCO_2$) or discretely (pH, DIC, and TA). Table 1 summarizes the methods used and the institutions that were involved in measurements during the test.

The multi-parameter flow-through CO2 system was located in the hydrolab of the ship attached to the uncontaminated underway seawater line. The ship underway water pump delivered seawater at a rate of 35-40 L $min_{-1}$. The seawater stream flowed through a 100 m long, 5 cm diameter Teflon-lined stainless steel tube. Transit time for the underway seawater stream between a bow intake 5m below the water line and the instruments in the hydrolab was about 2.5 minutes. Several underway instruments operated by different institutions used underway seawater for measurements of various surface seawater parameters. Unused seawater was discharged aft of the hydrolab. The seawater sample used for the system was teed off the sample pipe used by the AOML underway $pCO_2$ system (a gas/solution equilibrator connected to a Li—COR 6252 infrared analyzer). For the sampling system, surface seawater was pumped (via insulated Tygon tubing) through a plastic plate filter before entering the CTD for measurements of temperature and salinity. The sample stream was then diverted into the thermostated channels (25° C.) for measurements of pH, DIC and $fCO_2$.

The shipboard computing system (SCS) recorded underway fluorescence and thermos alinograph data obtained from a shipboard fluorometer and a thermosalinograph located in a seachest near the hull. The thermosalinograph data were used to convert our underway $fCO_2$ measurements at 25° C. to values at in-situ temperatures.

Figure 4:
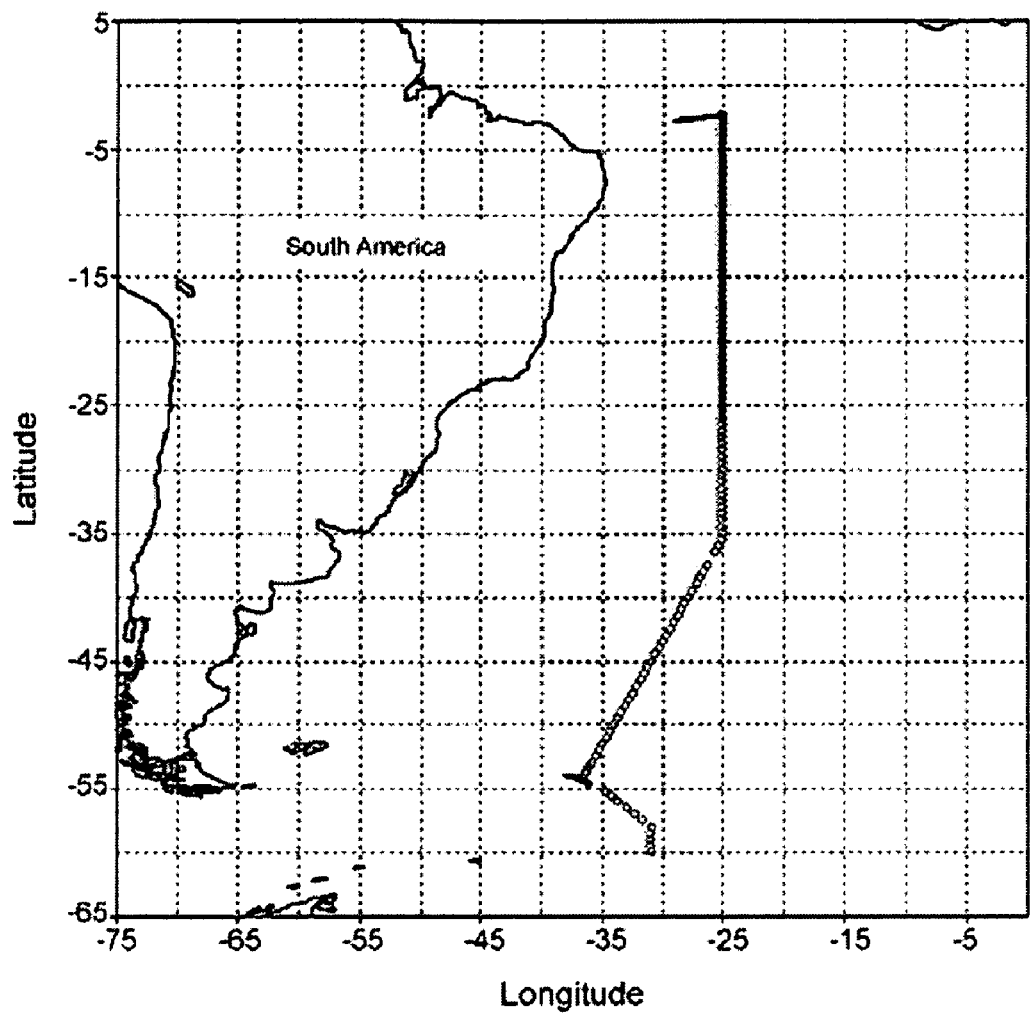
FIG. 4 shows the test track and sampling station locations. The circles indicate the hydrographic sampling stations, and the solid line show the track where underway measurements of $fCO_2$, DIC, and pH were obtained.

The multi-parameter flow-through $CO_2$ system performed well during testing. Contamination of the seawater sample line precluded comparisons with other measurements during the first half of the cruise. Even so, the three seawater channels produced $fCO_2$, DIC and pH measurements that were thermodynamically consistent. Data from the second half of the cruise (FIG. 4) are presented for direct comparison with other established methods.

Figure 7A:
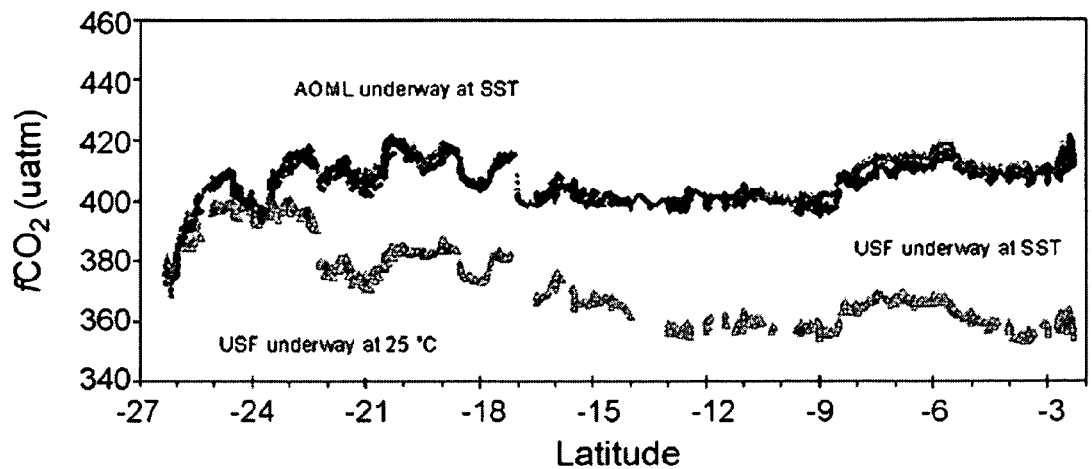
FIG. 7A is a comparison of the USF underway multi-parameter $fCO_2$ measurements with measurements obtained with established standard methods.

FIG. 7 shows surface $fCO_2$, DIC and pH underway measurements that cover the tropical and subtropical regions of the western South Atlantic Ocean from 26.3° S to 2.7° S. Surface $fCO_2$ at 25° C. varied from a little over 400 µatm at the center of the subtropical gyre to 350 µatm near the Equator (FIG. 7a).

Figure 7B:
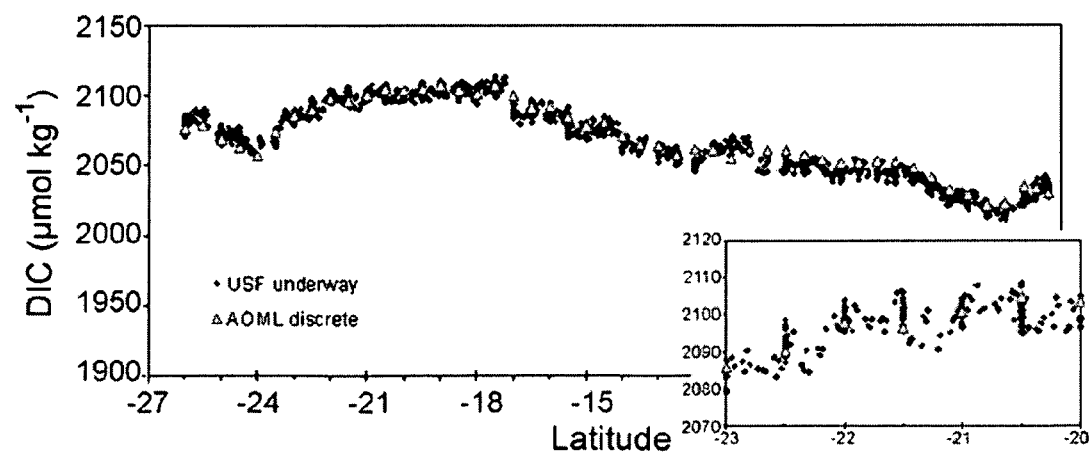
FIG. 7B is a comparison of the USF underway multi-parameter DIC measurements with measurements obtained with established standard methods. Insert represents DIC and pH measurements on a finer scale.
Figure 7C:
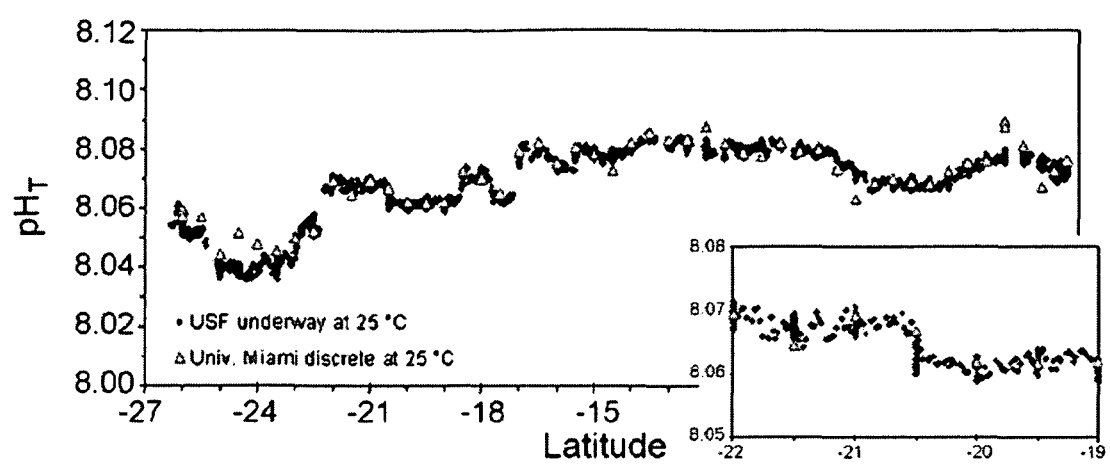
FIG. 7C is a comparison of the USF underway multi-parameter $pH_T$ measurements with measurements obtained with established standard methods. Insert represents DIC and pH measurements on a finer scale.

This represents a typical meridional variation of $fCO_2$ in this area under summer conditions at constant temperature (25° C.). DIC concentrations varied from ~2040 to more than 2110 µmol $kg^{-1}$ (FIG. 7b). DIC was strongly correlated with surface salinity (data not shown). Seawater pH at 25° C. showed, as expected, an inverse relationship with $fCO_2$ at 25° C., varying between 8.036 and 8.079 (FIG. 7c). DIC concentrations do not require corrections for comparison with discrete DIC measurements since DIC does not vary with temperature. Measurements of pH were obtained at 25° C., consistent with the measurement format of discrete pH measurements conducted independently. For $fCO_2$ measurements, temperature and water vapor corrections are required for comparison of our measurements at 25° C. with underway measurements obtained by the AOML underway system.

The AOML system uses a showerhead equilibrator to equilibrate sample water $CO_2$ with headspace air. This air is then dried prior to measurement with a Li—COR infrared $CO_2$ analyzer. The Li—COR system is calibrated using dry $CO_2$ gas, and measures dry $CO_2$ gas samples. Shipboard Li—COR measurements were then corrected to $fCO_2$ at in-situ temperature and 100% water vapor content. In contrast, the $fCO_2$ channel of our multi-parameter flow-through $CO_2$ system directly measures seawater samples at 25° C. For both calibrations using dry gas, and measurements with seawater, the $fCO_2$ of the internal indicator solution equals the $fCO_2$ of the gas or sample water equilibrated across the LCW at 25° C. For inter-comparisons with the NOAA AOML underway measurements, the $fCO_2$ results were corrected from 25° C. to field temperature using the temperature factor of 0.0423° $C.^{-1}$.

After temperature correction, the $fCO_2$ values obtained were in excellent agreement with the NOAA AOML underway $pCO_2$ system measurements (FIG. 7a). Underway DIC measurements also agreed well with discrete DIC measurements of surface water performed by the NOAA AOML (FIG. 7b). The pH measurements produced data in good agreement with the discrete pH values from surface sampling (FIG. 7c). Compared to sparse discrete surface measurements, the underway measurements exhibited much more detail in the spatial variation of sea surface DIC and pH along the test track (FIG. 7, including inserts). For both DIC and pH, approximately 30 autonomous measurements were obtained for each discrete measurement. In this context, it is important to note that the underway DIC and pH measurements show significant temporal variation at constant latitude (FIG. 7 inserts: latitudes −20.5, −21.0, −21.5°, etc) during the 3-5 hour required for profiling operations at each sampling station, while only one surface measurement was obtained via discrete sampling during this time.

Measurement Characteristics of the Multi-Parameter Flow-Through $CO_2$ System

Figure 5A:
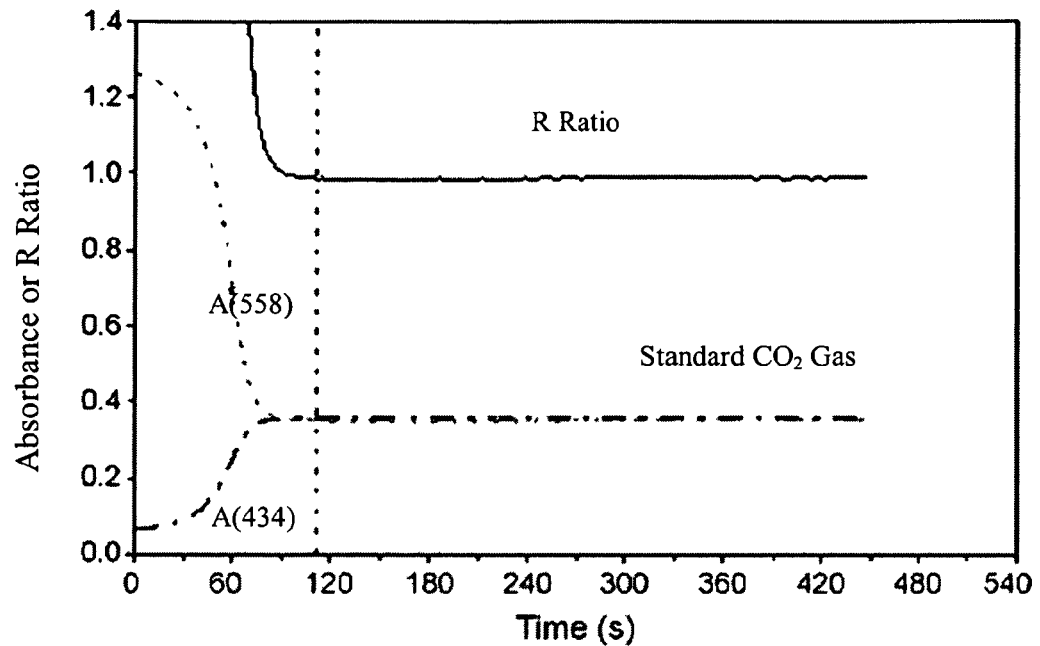
FIG. 5A is a graph showing curves of absorbance ratio (R) versus time of standard $CO_2$ gas using phenol red as the indicator during equilibration for the Teflon AF 2400 LCW optical cells.
Figure 5B:
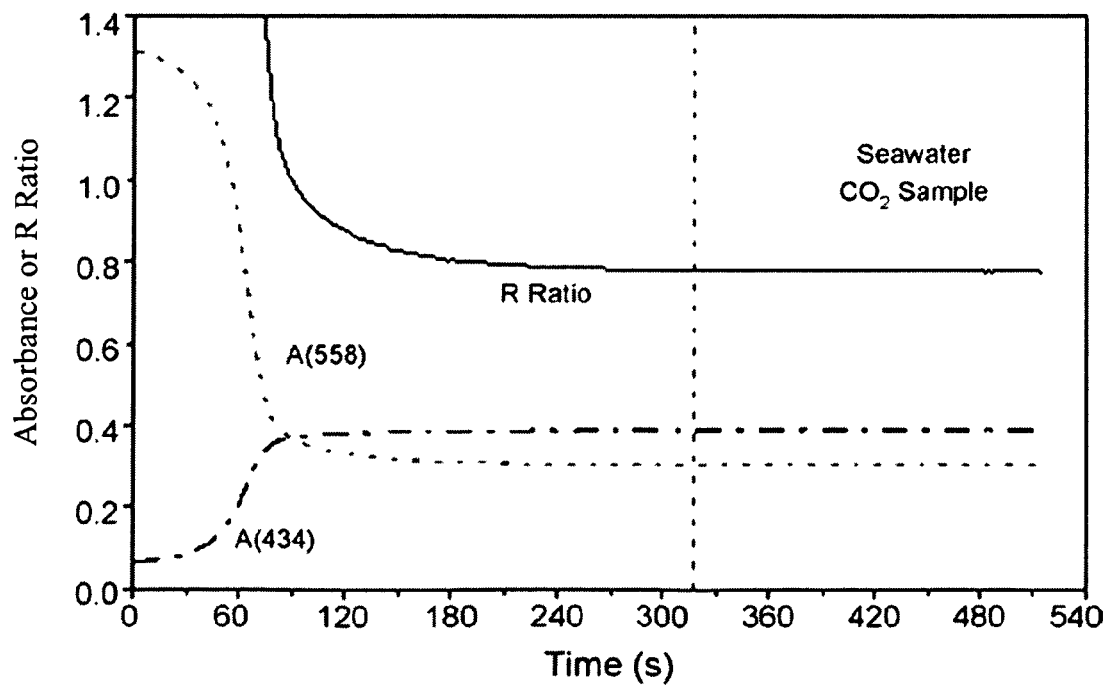
FIG. 5B is a graph showing curves of absorbance ratio (R) versus time of seawater $CO_2$ sample using phenol red as the indicator. The vertical dotted lines represent the time when the LCW cells reach equilibrium.
Figure 5C:
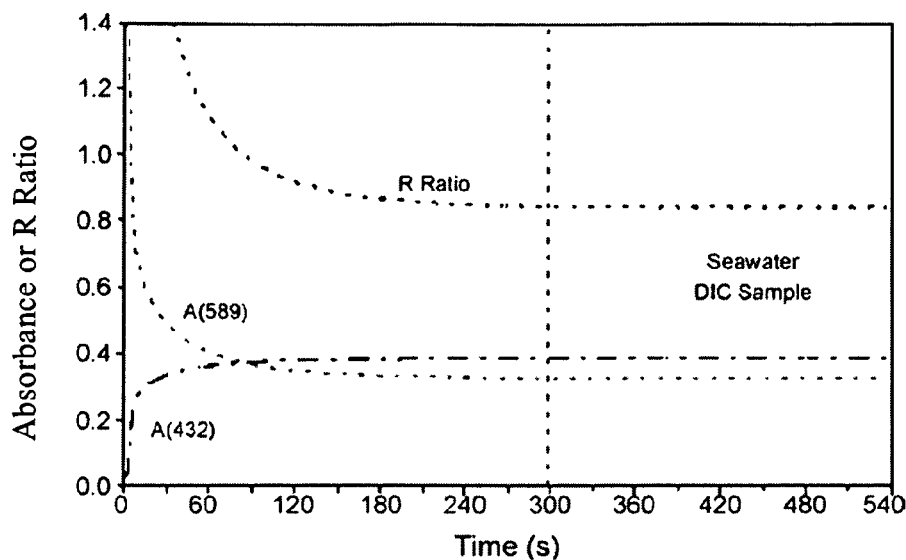
FIG. 5C is a graph showing curves of absorbance ratio (R) versus time seawater DIC sample using bromocresol purple as the indicator during equilibration for the Teflon AF 2400 LCW optical cells.

Since the time required for direct measurements of solution pH was negligible, the overall measurement frequency of the invention depends on the equilibration time required for $fCO_2$ and DIC measurements. Full equilibrium was achieved when no variation in R ratio (±0.001) was observed for longer periods of equilibration. The equilibration time for $fCO_2$ and DIC measurements depends on the volume of the internal indicator solution, the $CO_2$ gradient between the sample and the indicator solution, the wall thickness of the LCW capillary tubing, and the equilibration temperature. High frequency measurements were desirable to generate data with high temporal resolution. Using LCWs with thin walls and small internal volumes, approximately 2 minutes were required to obtain full equilibrium for a 354 µatm $CO_2$ standard gas (FIG. 5A). As shown in FIGS. 5B and 5C, the equilibration time for $fCO_2$ and DIC measurements in seawater was ~5 min. An equilibration time of 7 minutes was selected to ensure full equilibrium in all concentration ranges for $fCO_2$ and DIC measurements in natural water.

Figure 6:
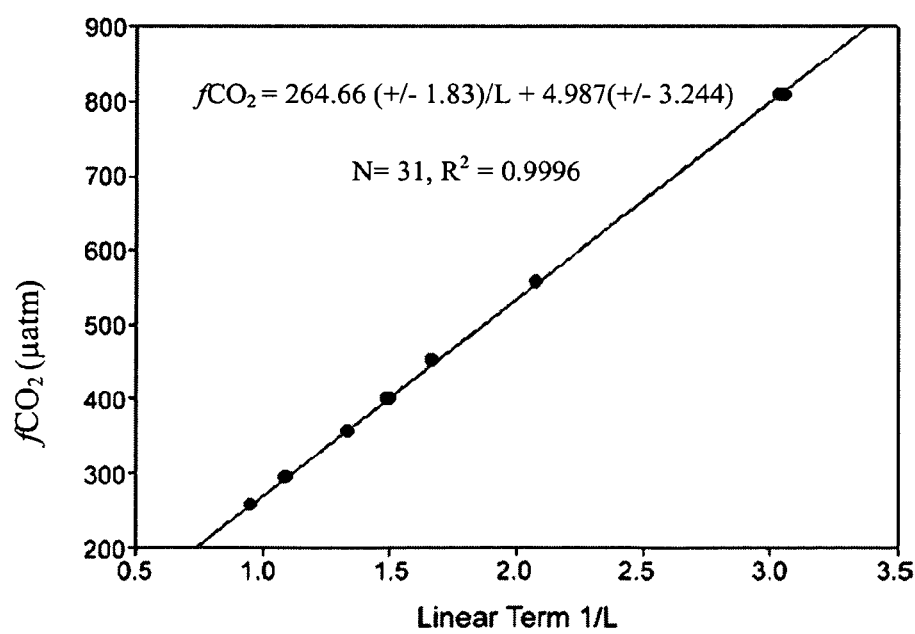
FIG. 6 is the calibration curve for the $f_cO_2$ channel The indicator solution consisted of 2 μM phenol red, 225 μmol$^{kg-1}$ total alkalinity ($_Na_{2C}O_3$), and 0.5 ml$^{L-1}$ 10% lauryl sulfate sodium salt. The numbers in parentheses in the linear equation denote 95% confidence intervals of the slope and intercept.

The $fCO_2$ calibration curve shown in FIG. 6 was linear as prescribed by Eq. (16). Each calibration curve generates a slope and an intercept appropriate to a particular batch of indicator solution made in the laboratory. The calibrated batch solution can then be used to measure $fCO_2$ samples in the field. Such calibrations eliminate stringent requirements for the accuracy of indicator solution total alkalinity because any uncertainty in the composition of the solution was built into the calibration slope and intercept. Furthermore, all other potential uncertainties, such as uncertainties in thermodynamic equilibrium constants, were also accommodated in the calibration process.

DIC calibration was conducted by repeated measurements of Certified Reference Materials (CRM). The constant B derived using Eq. (23) was then appropriate to a particular batch of indicator/alkalinity reagent solution. The uncertainty (one standard deviation) in the constant B was ~±0.0004 for DIC on the order of 2000-2150 µmol kg$^{-1}$. This was equivalent to an R ratio uncertainty of ~±0.001 and a DIC uncertainty of ~±1.9 µmol kg$^{-1}$. Similarly, the uncertainties of reagent composition and thermodynamic constants were then incorporated in the B constant. No calibration was required for pH measurements since all characteristics of thymol blue have been established previously. Accurate temperature control was critical for all measurements and calibrations since all parameters were measured at a defined constant temperature. Periodic temperature observations ensure that temperature variation was smaller than ±0.1° C.

The precisions of $fCO_2$ and DIC measurements using the multi-parameter flow-through $CO_2$ system were assessed by replicate measurements of standards in the laboratory. One standard deviation of the R ratios, directly measured for both $fCO_2$ and DIC channels, was on the order of ~0.001. This translates into different $fCO_2$ and DIC uncertainties along $fCO_2$ and DIC gradients.

Precision decreases with increasing $fCO_2$ and DIC. For example, the system can achieve a precision of ~0.5 µatm at 370 µatm $fCO_2$ and approximately 1 µatm at 650 µatm $fCO_2$. As such, the relative precision for $fCO_2$ measurements was approximately ±0.14%. For DIC measurements, the precision was ~1.4 µmol kg$_{-1}$ for a DIC concentration of 1740 µmol kg$^{-1}$, and ~2.4 at a DIC concentration of 2250 µmol kg$^{-1}$. In this case (DIC measurements), the relative precision was on the order of ±0.09%. Such precisions for $fCO_2$ and DIC measurements were comparable to the precisions of established methods. Replicate analysis indicates that the pH measurement precision of the current instrumentation was better than 0.001 pH units. This was close to the precision of well-documented discrete spectrophotometric pH measurements (±0.0004) obtained on research vessels.

Field Precision and Accuracy

Two approaches were used to evaluate the field precision of the underway system. In the first approach, the corrected data in FIG. 7 were smoothed by taking running averages (every 5 data points). Residuals of the data relative to the running averages were then calculated to evaluate the precision of the instrument.

Figure 8A:
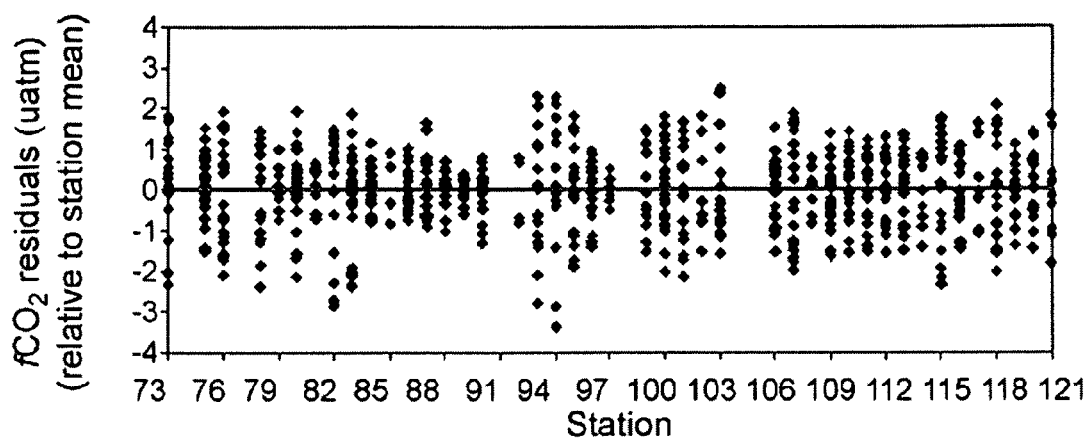
FIG. 8A shows residual plots relative to the mean underway measurements at each station for $fCO_2$ at 25° C.
Figure 8B:
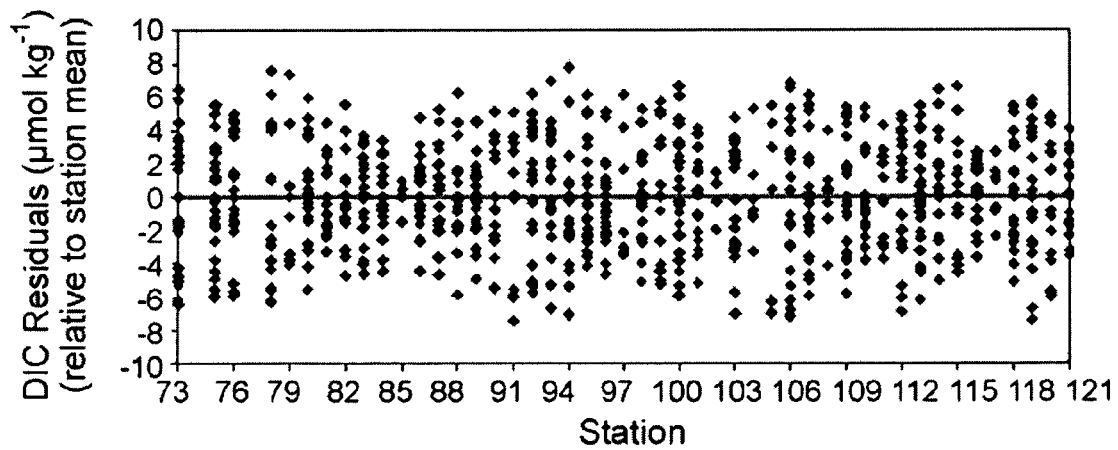
FIG. 8B shows residual plots relative to the mean underway measurements at each station for DIC at 25° C.
Figure 8C:
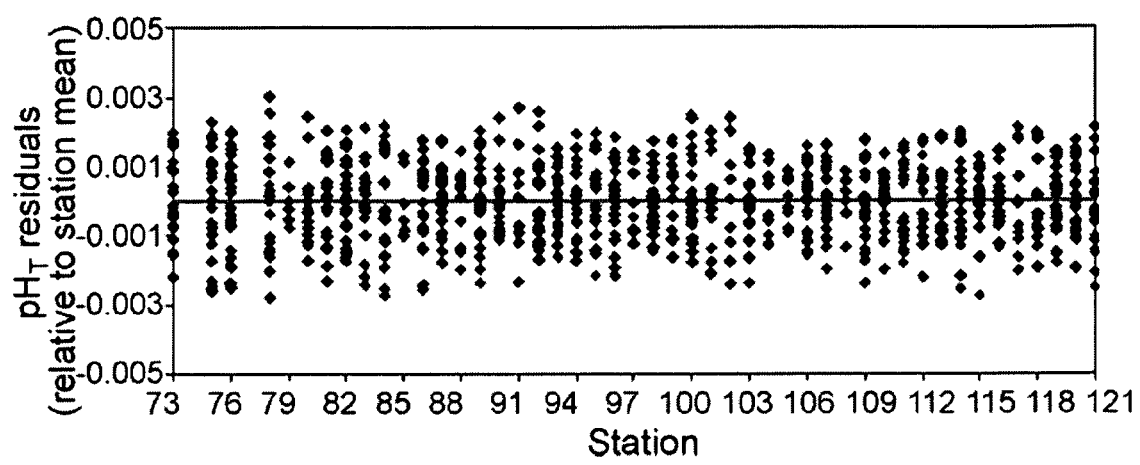
FIG. 8C shows residual plots relative to the mean underway measurements at each station for $pH_T$ at 25° C.

For the $fCO_2$ channel, the mean residual of individual observations relative to the running average was −0.005 µatm with a standard deviation (1σ) of 0.91 µatm (N=1503). The DIC measurements achieved a mean residual of 0.003 µmol kg$^{-1}$ with σ=2.4 µmol kg$^{-1}$ (N=1534). For pH measurements, the mean residual and one standard deviation (N=1808) were 0.0000 and 0.00083. This evaluation reflects a short-term variation in the underway measurements since the running averages were taken for every 5 adjacent data points (within an hour). For the second approach, the residuals relative to the mean of the underway measurements were calculated at each station where the ship was stationary (3-5 h) (FIG. 8). The assumption in this approach is that surface seawater does not experience appreciable changes for the three measured parameters during the time at stations. The mean residuals for $fCO_2$, DIC, and pH calculated using this approach were 0.004±0.95 µatm (N=740), −0.03±3.2 µmol kg-1 (N=787), and 0.0000±0.0011 pH units (N=894), respectively.

The first approach yielded slightly better precisions for all three measurements, probably because it uses short-term averages. If averages are taken for a longer period of time, natural temporal and spatial variations for these measured parameters may contribute to an appearance of decreasing precision. Although both evaluations reveal that the field precisions of fCO2 and DIC measurements are somewhat lower than those achieved under laboratory conditions, they still exhibit high sensitivity and are comparable to other established shipboard methods (Table 1).

The pH measurements achieved a precision of near 0.001, which is in excellent agreement with laboratory evaluations, and compares favorably with other shipboard and in-situ pH measurements.

Figure 9A:
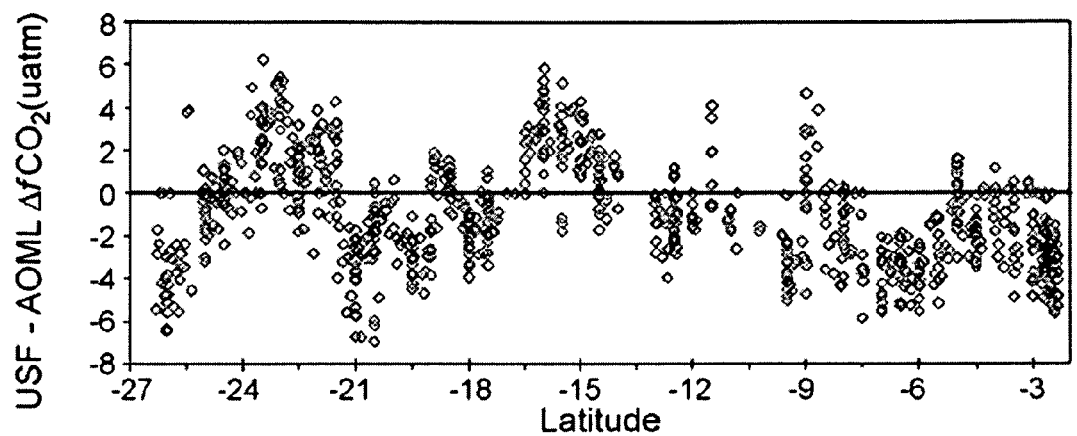
FIG. 9A shows the measurement differences between the multi-parameter flow-through $CO_2$ system and AOML $\Delta fCO_2$ residual plot at sea surface temperature.
Figure 9B:
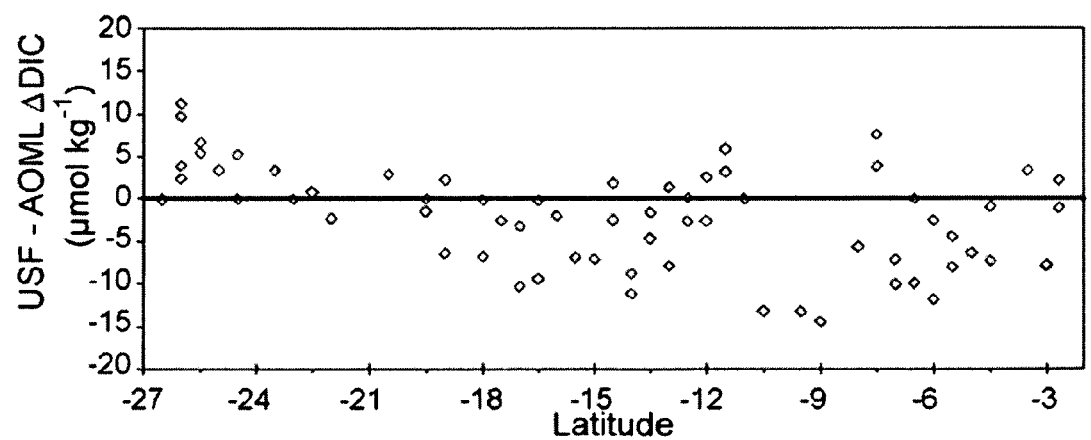
FIG. 9B shows the measurement differences between the multi-parameter flow-through $CO_2$ system and AOML $\Delta$DIC residual plot.
Figure 9C:
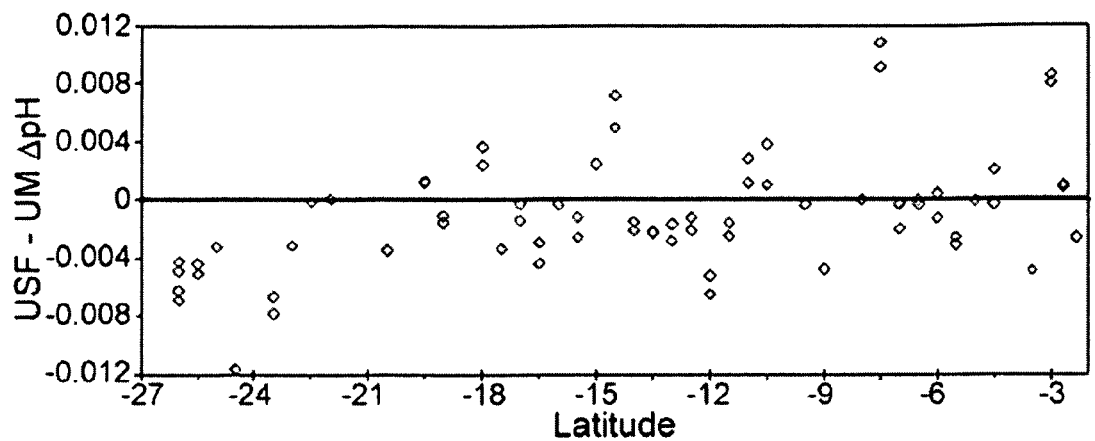
FIG. 9C shows the measurement differences between the multi-parameter flow-through $CO_2$ system and UM $\Delta$pH residual plot at sea surface temperature.

Field measurement accuracies were accessed by directly comparing the differences between the data and data obtained by NOAA (AOML) and the University of Miami using established methods (FIG. 9). The different data sets were coordinated based on time stamps to form data pairs. A weak periodic trend of $fCO_2$ residuals is observed in FIG. 9a. Further exploration of the trend did not reveal any significant association between $fCO_2$ residuals and known potential causative factors (e.g. temperature corrections and calibration schedule). In general, FIG. 9 indicates that residuals between the underway measurements and the AOML and UM measurements do not show substantial systematic trends. This suggests that any systematic errors in the measurements of $fCO_2$, DIC, and pH are minor Based on the assessment shown in FIG. 9, the $fCO_2$ measurements differed from theAOML underway measurements by a mean of 1.0 µatm with σ=2.5 µatm (N=947). For DIC and pH, mean differences between the measurements and discrete measurements were 2.2±6.0 (DIC, one standard deviation) µmol kg$^{-1}$ (N=64) and 0.0012±0.0042 (pH, one standard deviation) (N=68). These assessments demonstrate that the multi-parameter flow-through $CO_2$ system can provide $fCO_2$, DIC, and pH measurements that are in excellent agreement with existing standard methods. Table 2 summarizes all major characteristics and features of the current system.

The underway measurements of $fCO_2$ and DIC used calibration standards identical to those used in discrete DIC measurements and non-dispersive IR measurements of $fCO_2$ (identical CRM and $CO_2$ standard gases). The agreement between the flow-through measurements and the conventional $fCO_2$ and DIC measurements discussed above is thus an expression of flow-through system accuracy defined in terms of consistency with established methods used in the field. For pH measurements, different indicators were used for flow-through measurements (thymol blue) and discrete measurements (m-cresol purple). This implies that the pH offset (0.0012±0.0042) in FIG. 9c includes contributions from independent calibrations of the two indicators.

Variability and Internal Consistency

The field precisions of the $fCO_2$, DIC, and pH measurements estimated using the two discussed methods are about one half of the field agreement ranges calculated by directly comparing the measurements with other established measurements (Table 2). The measurement variability resulting from the instruments' inherent noise therefore only accounts for ~50% of the variability observed in FIG. 9. The rest of the variability or uncertainty of the measurements depicted in FIG. 9 may be attributable to various external sources. Coordinating the measurements with other measurements to make comparisons generates uncertainty for all three measurements due to potential mismatches of time.

For DIC and pH measurements, the system measured the underway water pumped from the bow of the ship, while discrete measurements obtained water samples from CTD/Rosette casts. Measurement of different samples adds uncertainty to data comparisons. A few data from the discrete pH measurements were considerably scattered relative to the underway pH measurements (FIG. 7c). Observed differences were greater than 0.01 pH units. For these data, however, no apparent discrepancies were observed for either $fCO_2$ or DIC measurements (FIG. 7a and b). Moreover, thermodynamic calculation indicates that pH calculated from underway DIC and $fCO_2$ measurements did not show large pH scatter at these points. As such, it is believed that sampling/analysis errors during discrete pH measurements contributed to the observed differences.

Temperature corrections are required for comparison of the $fCO_2$ dataset (25° C.) with the AOML dataset (in-situ temperature). For the shipboard versus in-situ temperature differences encountered (0.2-3.6° C.), a temperature correction of 0.0423±0.0002° C.−1 would introduce <1.0 µatm uncertainty at the fCO2 levels observed in this study. Other corrections, involving thermodynamic calculations and various temperature/salinity dependent constants, can also introduce errors in data comparisons. The residuals in FIG. 9 include contributions from both the instrumental methodologies and the methodologies used for conventional shipboard $fCO_2$, DIC and pH measurements. Consequently, it is reasonable to suppose that the Table 2 summary of system measurement quality reflects both the inherent characteristics of the flow-through $CO_2$ system measurements and contributions to imprecision and inaccuracy from a variety of additional sources.

Figure 10:
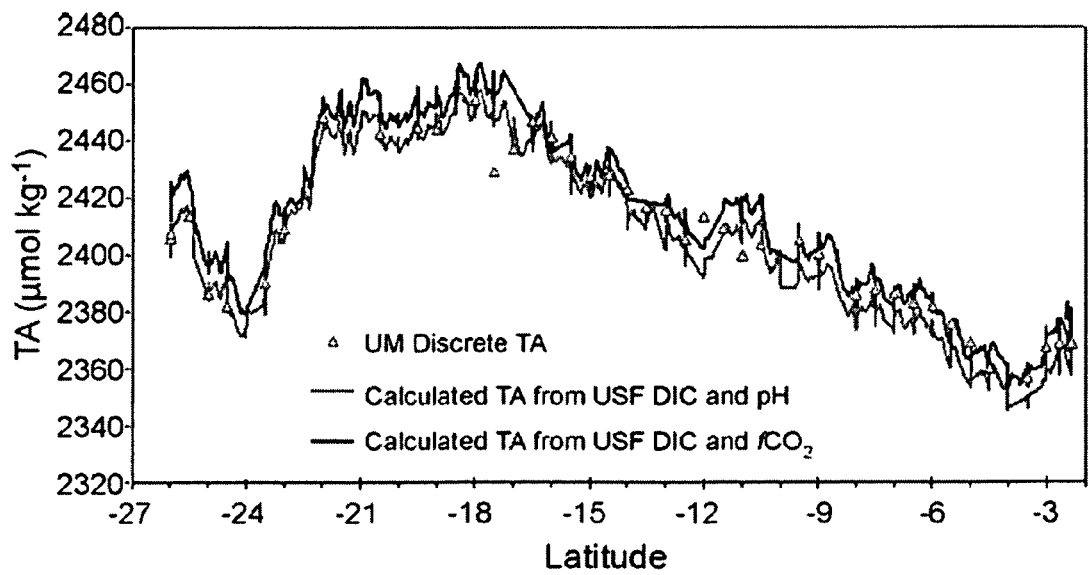
FIG. 10 is a comparison of UM discrete TA measurements and TA calculated from DIC-pH and DIC-$fCO_2$ underway data pairs.

Thermodynamic calculations using underway measurements of $fCO_2$, DIC, and pH were performed to examine the internal consistency of paired measurements. DIC-pH and DIC-$fCO_2$ data pairs were used to calculate TA via the $CO_2$SYS program (http://cdiac.ornl.gov/oceans/co2rprt.html) of E. Lewis, D. W. R. Wallace and K. M. Johnson (Brookhaven National Laboratory, NY). Results are presented in FIG. 10. The calculated TA from either the USF DIC-pH pair or the USF DIC-fCO2 pair is in good agreement with the UM discrete measurements (FIG. 10).

A mean difference of 3.0-3.2 µmol kg$^{-1}$ with a standard deviation of 6.8-6.9 µmol kg$^{-1}$ was obtained in this comparison. Residuals between discrete TA measurements and calculated TA values did not show a significant trend (data not shown). Thus, observed differences between measured and calculated TA were consistent throughout the test. The deviations of calculated TA values from discrete measurements in FIG. 10 reflect a combined influence of measurement variations and imperfections in thermodynamic models.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween. Now that the invention has been described,

What is claimed is:

1. A flow-through $CO_2$ measurement device, comprising:
a first optical cell having a sample inlet and reagent inlet;
a second optical cell having a sample inlet and reagent inlet;
a third optical cell having a sample inlet and reagent inlet;
an acid reservoir, a pH dye reservoir, an $fCO_2$ dye reservoir, a DIC dye reservoir, an $fCO_2$ reference solution reservoir, a DIC reference solution reservoir;
a water sample source;
a water-sample pump in fluid communication between the water source and respective sample inlets of the first, second and third optical cells;
a second pump in fluid communication between the acid reservoir and the sample inlet of the second optical cell;
a third pump in fluid communication between the pH dye reservoir and the sample inlet of the third optical cell;
a fourth pump in fluid communication between the $fCO_2$ dye reservoir and the reagent inlet of the first optical cell and in fluid communication between the DIC dye reservoir and the reagent inlet of the second optical cell; and
a fifth pump in fluid communication between the $fCO_2$ reference solution reservoir and the reagent inlet of the first optical cell and in fluid communication between the DIC reference solution reservoir and the reagent inlet of the second optical cell.

2. The device of claim 1, further comprising:
an in-line mixer disposed between the second pump and the sample inlet of the second optical cell; and
an in-line mixer disposed between the third pump and the sample inlet of the third optical cell.

3. The device of claim 1, further comprising:
a thermal equilibration coil disposed between the first pump and the sample inlet of the first optical cell;
a thermal equilibration coil disposed between the second pump and the sample inlet of the second optical cell; and
a thermal equilibration coil disposed between the third pump and the sample inlet of the third optical cell.

4. The device of claim 1, further comprising:
a plurality of valves disposed between the fourth pump and the reagent inlet of the first and second spectrometers; and
a plurality of valves disposed between the fifth pump and the reagent inlet of the first and second spectrometers.

5. The device of claim 1, further comprising:
a plurality of debubblers disposed between the fourth pump and the reagent inlet of the first and second spectrometers; and
a plurality of debubblers disposed between the fifth pump and the reagent inlet of the first and second spectrometers.

6. The device of claim 1, further comprising:
a plurality of thermal equilibration coils between the fourth pump the reagent inlet of the first and second spectrometers; and
a plurality of thermal equilibration coils disposed between the fourth pump the reagent inlet of the first and second spectrometers.

7. The device of claim 1, further comprising:
a light source communicatively coupled to the first, second and third optical cells; and
a first spectrometer communicatively coupled to the first optical cell;
a second spectrometer communicatively coupled to the second optical cell; and
a third spectrometer communicatively coupled to the third optical cell.

8. The device of claim 7, wherein the first, second and third spectrometers are disposed in a thermostated chamber.

9. The device of claim 7, further comprising:
said first optical cell including a liquid core waveguide disposed between the light source and the first spectrometer; and
said second optical cell including a liquid core waveguide disposed between the light source and the second spectrometer.

10. The device of claim 1, further comprising a thermostated water bath adapted to receive the optical cells.

11. The device of claim 1, further comprising a conductivity/temperature/depth (CTD) profiler between the water sample source and the first pump.

* * * * *

UNITED STATES PATENT AND TRADEMARK OFFICE
CERTIFICATE OF CORRECTION

| | | |
|---|---|---|
| PATENT NO. | : 8,077,311 B1 | Page 1 of 1 |
| APPLICATION NO. | : 12/108953 | |
| DATED | : December 13, 2011 | |
| INVENTOR(S) | : Robert H. Byrne, Eric Kaltenbacher and Xuewu Liu | |

It is certified that error appears in the above-identified patent and that said Letters Patent is hereby corrected as shown below:

In the Specification

Column 1, lines 16-19, should read:

This invention was made with government support under Grant Numbers: NA04OAR4310096, AB133R03CN0091, NA05OAR4601143 awarded by The National Oceanic and Atmospheric Administration. The government has certain rights in the invention.

Signed and Sealed this
Twentieth Day of October, 2015

Michelle K. Lee
*Director of the United States Patent and Trademark Office*